United States Patent [19]
Yamamoto et al.

[11] Patent Number: 6,079,284
[45] Date of Patent: Jun. 27, 2000

[54] VISUAL INSPECTION APPARATUS FOR TABLETS

[75] Inventors: Taizo Yamamoto, Osaka; Motohiro Yagyu, Nara-ken, both of Japan

[73] Assignee: Shinogi Qualicaps Co., Ltd., Nara-ken, Japan

[21] Appl. No.: 09/129,679

[22] Filed: Aug. 6, 1998

[30] Foreign Application Priority Data

Aug. 6, 1997 [JP] Japan .................................. 9-224392

[51] Int. Cl.$^7$ .................................................. G01N 15/02
[52] U.S. Cl. ............................................................ 73/865.8
[58] Field of Search .................................. 73/865.8, 800

[56] References Cited

U.S. PATENT DOCUMENTS

| | | | |
|---|---|---|---|
| 3,709,598 | 1/1973 | Vandenberg et al. | 356/428 |
| 5,085,510 | 2/1992 | Mitchell | 356/237 |
| 5,555,768 | 9/1996 | Shaffer et al. | 73/865.8 |
| 5,661,249 | 8/1997 | Rupp et al. | 73/865.8 |
| 5,878,868 | 3/1999 | Gotoh et al. | 198/689.1 |

*Primary Examiner*—Max Noori
*Attorney, Agent, or Firm*—Birch, Stewart, Kolasch & Birch, LLP

[57] ABSTRACT

There is provided a visual inspection apparatus wherein in the case where tablets are held on the outer peripheral surface of the right side inspection drum to be carried, the tablets are photographed during the carriage to thereby obtain the right side images, the tablets are delivered with the right side reversed to the wrong side from the right side inspection drum to the wrong side inspection drum, the tablets are carried while being held on the outer peripheral surface of the wrong side inspection drum, the tablets are photographed during carriage to thereby obtain the wrong side images, and when the visual inspection of the right side and the wrong side of the tablets is carried out based on the obtained right side image and the wrong side image, the tablets are carried stably so that the excellent right side image and the wrong side image can be positively obtained, securing the tablets not to damage during carriage and delivery of tablets, and even in the case where tablets to be inspected are changed, inspection can be carried out without replacing the right side inspection drum and the wrong side inspection drum.

7 Claims, 12 Drawing Sheets

FIG.4-A
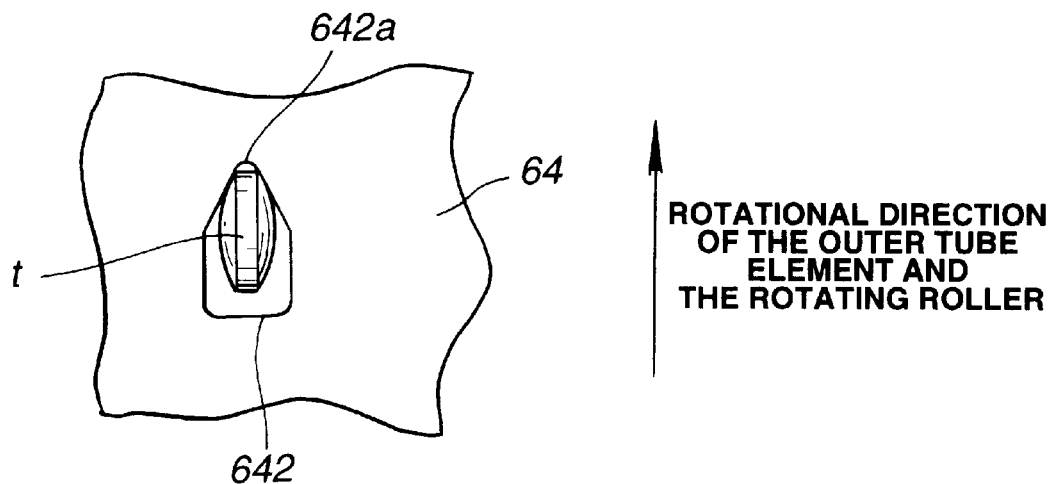
ROTATIONAL DIRECTION OF THE OUTER TUBE ELEMENT AND THE ROTATING ROLLER
FIG.4-B
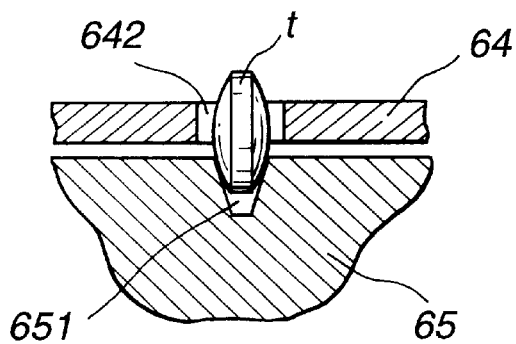

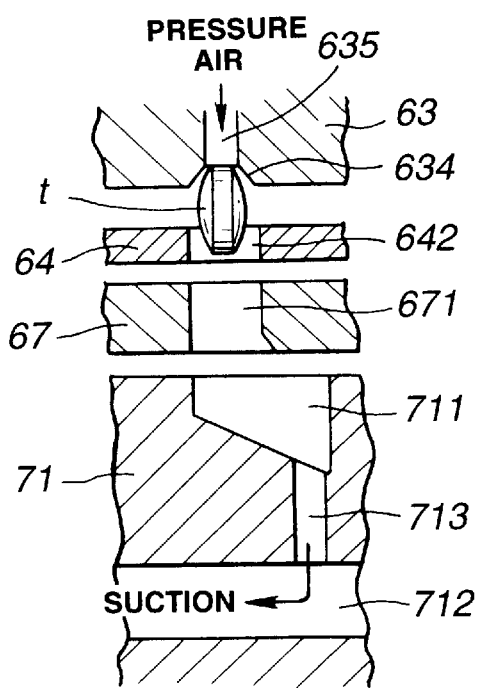
FIG.5-A
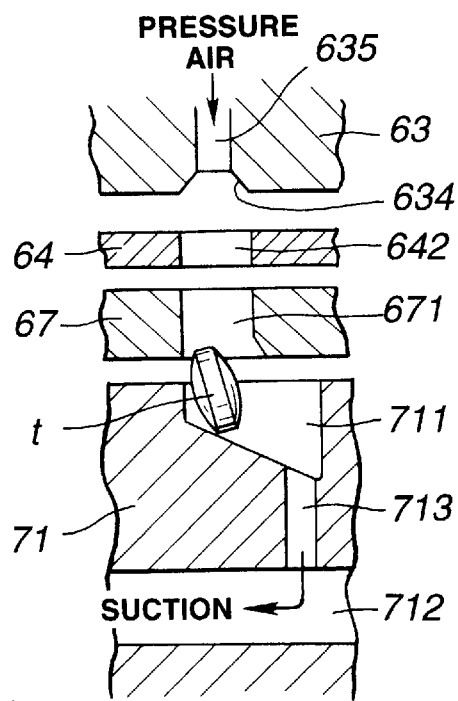
FIG.5-B
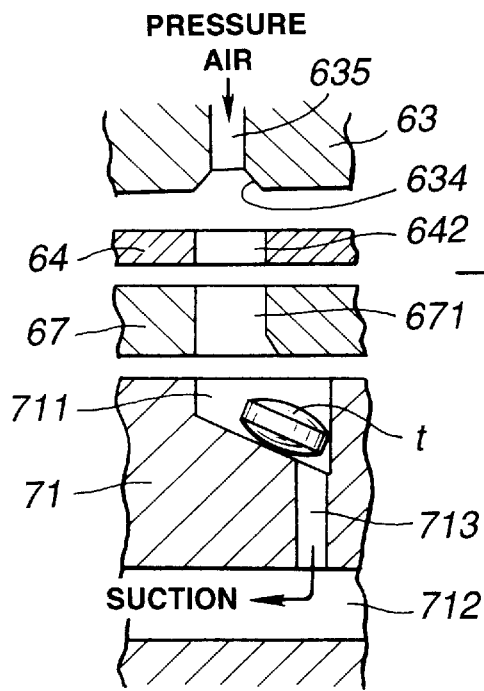
FIG.5-C
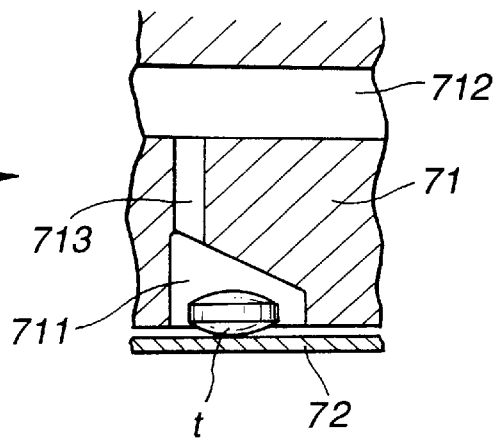
FIG.5-D

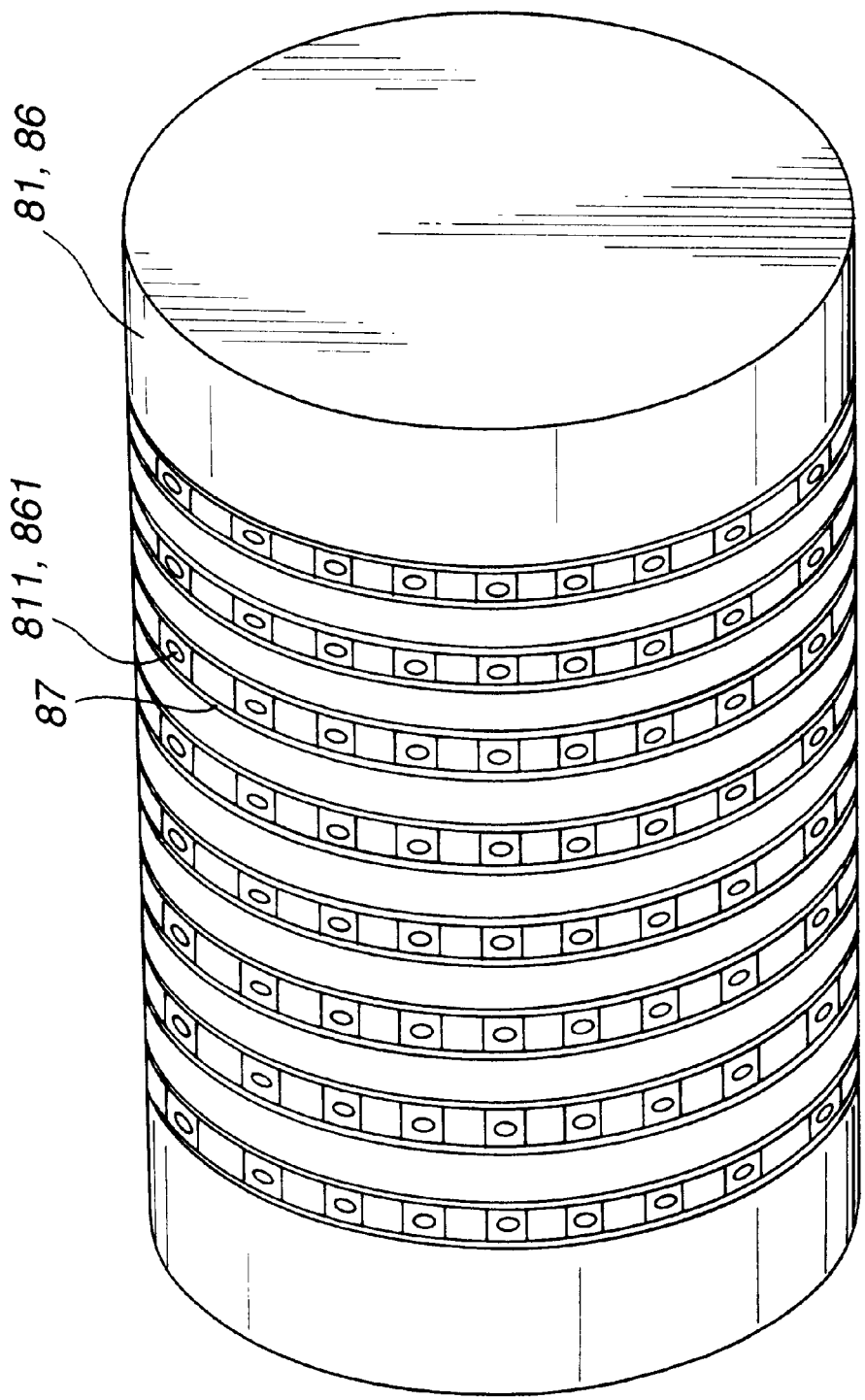

FIG.8-A
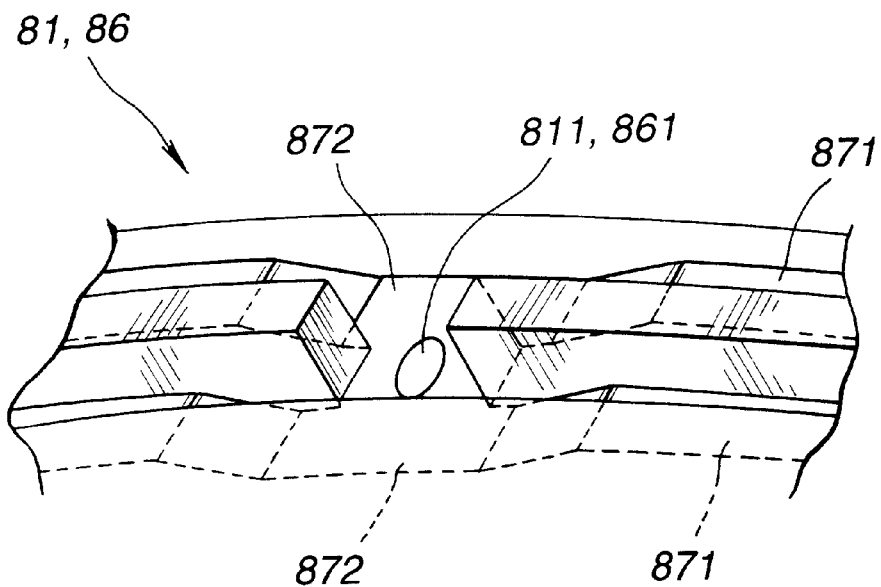
FIG.8-B
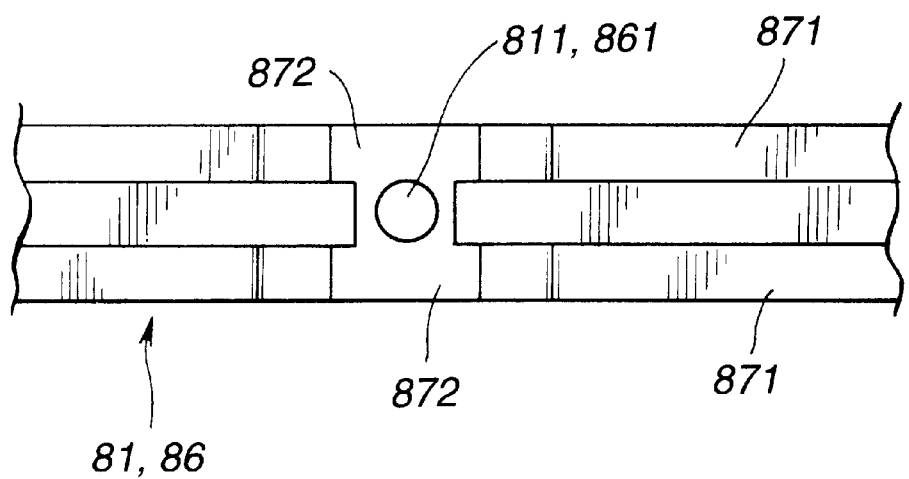

FIG.9-A
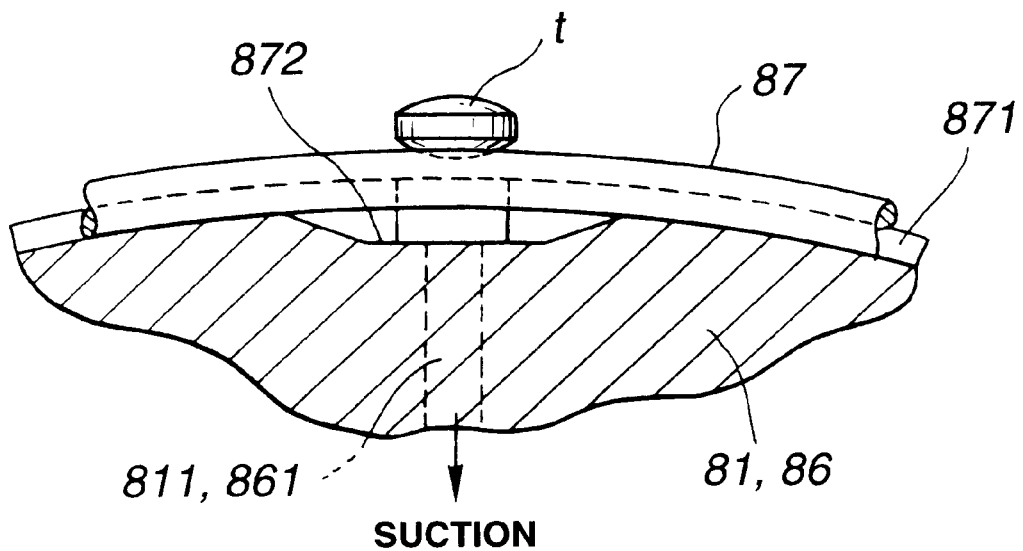
FIG.9-B
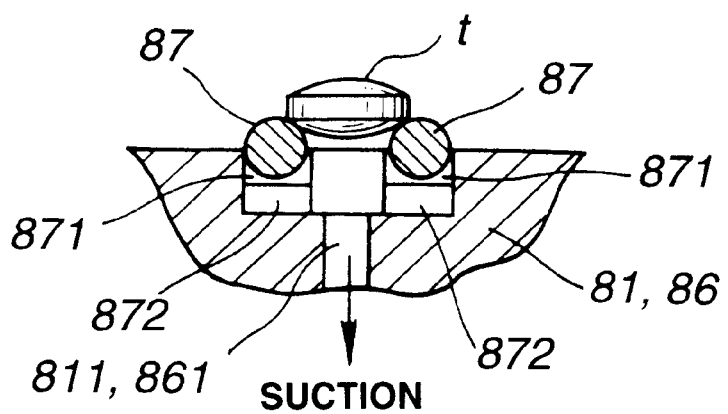

VISUAL INSPECTION APPARATUS FOR TABLETS

BACKGROUND OF THE INVENTION

The present invention relates to a visual inspection apparatus for tablets comprising the right side inspection drum for holding tablets on the outer peripheral surface and being rotated at fixed speeds to thereby carry the tablets, the wrong side inspection drum for receiving the tablets from the right side inspection drum to hold the tablets on the outer peripheral surface in the inverted state and being rotated at fixed speeds to thereby carry the tablets, and the right side imaging device and the wrong side imaging device for photographing the tablets carried while being held by the right side inspection drum and the wrong side inspection drum to take the right side images and the wrong side images of the tablets, the apparatus inspecting the rejected appearance of the right side and the wrong side of the tablets from the obtained right side image and the wrong side image.

In the past, the visual inspection for inspecting whether adhesion of foreign matter on tablets, contamination and deformation such as break and crack, or defects such as rejected print occur or not is automatically carried out using a visual inspection apparatus. In the case where flat-shaped tablets are automatically inspected using such a visual inspection apparatus as described, there is normally employed a method for processing images obtained by photographing tablets with a camera during carriage to thereby detect the defects. In the case of the flat-shaped tablets, it is necessary to photograph them from three different angles, i.e. the side (peripheral edge), the right side and the wrong side for inspection. To this end, it is necessary to control the attitude of tablets accurately in order to positively photograph the places to be inspected, and necessary to change, during carriage, the attitude of tablets according to three photographing places, i.e. the side (peripheral edge), the right side and the wrong side.

As such a visual inspection apparatus for tablets, an inspection apparatus shown in FIG. 11 can be specifically illustrated.

This visual inspection apparatus comprises a tablet supply section 1 for supplying a number of flat-shaped tablets (hereinafter referred to as tablets) stored in a hopper 11 to an inspection mechanism section, a side inspection section 2 comprising a side inspection drum 21 and a side imaging device 22, an attitude conversion section 3 having an attitude conversion drum 31, a both-side (the right and the wrong side) inspection section 4 having the right side inspection drum 41, the wrong side inspection drum 42, the right side imaging device 43 and the wrong side imaging device 44, a classification section 5 having a classification drum 51, an excellent article recovering conveyor 52 and a rejected article recovering can 53, and a decision section for processing images obtained from the three imaging devices 22, 43 and 44 to detect the presence or absence of the rejected appearance though not shown. In the figure, reference numerals 221, 431 and 441 designate cameras, and numerals 222, 432 and 442 designate illumination devices.

The visual inspection by the above-described visual inspection apparatus is carried out in the following procedures:

(1) A number of tablets supplied at random from the hopper 11 are continuously supplied to the side inspection drum 21 of the side inspection section 2 in a upright state with a diametrical direction vertically set by the tablet supply section 1 (hereinafter referred merely to as "upright state");

(2) the tablets are stored in the upright state into a holding pocket of the side inspection drum 21, the tablets are carried downward by the rotation of the drum 21, and the tablets are photographed by the right side imaging device 22 while rotating the tablets being carried within the holding pocket to obtain the image of the whole side of the tablets;

(3) the tablets are transferred to the attitude conversion drum 31 of the attitude conversion section 3, the tablets in the upright state are laid down laterally by the drum 31 into a prostrated state with the thickness direction vertically set (hereinafter merely referred to as "prostrated state"), after which the tablets are delivered to the right side inspection drum 41 of the both-side inspection section 4;

(4) the tablets are stored in the prostrated state into a tablet storing pocket formed on the surface of the right side inspection drum 41, the tablets are carried downward by the rotation of the drum 41, and the tablets being carried are photographed by the imaging device 43 to obtain the right side images of the tablets;

(5) the tablets are delivered to the wrong side inspection drum 42 and stored in the inverted prostrated state into the tablet storing pocket of the wrong side inspection drum 42, the tablets are carried downward by the rotation of the drum 42, and the tablets being carried are photographed by the imaging device 44 to obtain the wrong side images of the tablets; and (6) then, the tablets are transferred to the classification drum 51 of the classification section 5, the rejected tablets are transferred to the rejected article recovering can 53 according to the inspection results obtained by processing the side images, the right side images and the wrong side images, and the excellent tablets are transferred onto the excellent article recovering conveyor 52 and carried to the recovering conveyor c for recovery.

However, in the above-described visual inspection apparatus, the tablets being held on the outer peripheral surfaces of the right side inspection drum 41 and the wrong side inspection drum 42 are so unstable that the images are sometimes not always taken stably, and in addition, when the tablets are delivered between the right side inspection drum 41 and the wrong side inspection drum 42, damages such as crack or break sometimes occur.

More specifically, in both the above-described right side inspection drum 41 and the wrong side inspection drum 42, tablets t are stored in tablet storing pockets 411, 421 provided in the outer peripheral surfaces of the drums 41, 42, and the tablets t are held within the pockets 411, 421 by suction of suction holes 412, 422, as shown in FIG. 12. In this case, the pockets 411, 421 are formed to be slightly larger than the tablets t in order to smoothly effect the delivery of the tablets t. Therefore, the tablets t stored in these pockets 411, 421 sometimes cause shakes within the pockets 411, 412. Eventually, it is sometimes not possible to obtain good images. Further, since the tablets are photographed in the state that they are stored in the recessed pockets 411, 421, shade tends to occur on the tablets during the photographing, by which obtaining the good images is sometimes blocked.

Further, the tablets t are delivered from the right side inspection drum 41 to the wrong side inspection drum 42 by pressure air jetted from a suction hole 412, when the pockets 411 of the right side inspection drum 41 are registered with the pockets 421 of the wrong side inspection drum 42, to extrude the tablets t from the pockets 411 of the right side inspection drum 41. Thus, the tablets t are attracted into the pockets 421 of the wrong side inspection drum 42 to move. At that time, when the tablets t move between both the drums 41 and 42 formed of metal such as stainless steel, a great load or shock is applied to the tablets t so that damages such as crack or break sometimes occur in the tablets t.

Furthermore, it is necessary to set the tablet storing pockets 411, 421 of the right side inspection drum 41 and the wrong side inspection drum 42 to proper size according to the size and shape of the tablets t in order to smoothly effect the delivery of the tablets t, and to stably locate them without shake for carriage. Therefore, when the kind (size and thickness) of the tablets subjected to inspection is changed, the right side inspection drum 41 and the wrong side inspection drum 42 need to be replaced with those having the tablet storing pockets 411, 421 of proper size on all such occasions. When the tablets to be inspected are changed, extremely cumbersome operation is necessary.

SUMMARY OF THE INVENTION

The present invention has been achieved in view of the foregoing. It is an object of the invention to provide a visual inspection apparatus wherein in the case where tablets are held on the outer peripheral surface of the right side inspection drum and carried, the tablets are photographed during the carriage to thereby obtain the right side images. The tablets are then delivered with the right side reversed to the wrong side from the right side inspection drum to the wrong side inspection drum, while being held on the outer peripheral surface of the wrong side inspection drum, the tablets are photographed during carriage to thereby obtain the wrong side image. In order to carry out the visual inspection of the right side and the wrong side of the from the obtained right side image and the wrong side image, the tablets are carried stably so that the excellent right side image and the wrong side image can be positively obtained without damaging the tablets during carriage and delivery. Even in the case where tablets to be inspected are changed, inspection can be carried out without replacing the right side inspection drum and the wrong side inspection drum.

For achieving the aforementioned object, the present invention provides a visual inspection apparatus comprising: the right side inspection drum for holding flat-shaped tablets on the outer peripheral surface in a prostrated state with the thickness direction vertically set and being rotated at fixed speeds to thereby carry the tablets; the wrong side inspection drum disposed in the state that the outer peripheral surface thereof is placed close to the right side inspection drum, receiving the tablets from the right side inspection drum to hold the tablets on the outer peripheral surface in the inverted state and being rotated at fixed speeds to carry the tablets; the right side imaging device for photographing the tablets held on the surface of the right side inspection drum to take the right side image of the tablets; and the wrong side imaging device for photographing the tablets held on the outer peripheral surface of the wrong side inspection drum to take the wrong side image of the tablets; both the right side inspection drum and the wrong side inspection drum comprising an array of numbers of suction holes and formed on the outer peripheral surfaces of the drums; and a plurality of rubber bands wound along the peripheral direction with the suction holes put therebetween, characterized in that the tablets are adsorbed across two rubber bands by absorptivity from the suction holes.

In the visual inspection apparatus according to the present invention, tablets t are held in a prostrated state on the outer peripheral surface of the right side inspection drum and carried, the tablets are photographed by the right side imaging device to take the right side images of the tablets. The tablets t are then delivered to the wrong side inspection drum which is disposed in a state that the outer peripheral surface thereof is placed close to the right side inspection drum and rotated to hold the tablets in an inverted state on the outer peripheral surface of the wrong side inspection drum, and the tablets t are photographed by the wrong side imaging device to take the wrong side images of the tablets t to thereby carry out the visual inspection of the right side and the wrong side of the tablets.

In this case, according to the visual inspection apparatus of the present invention, the tablets are adsorbed on the rubber bands wound around the outer peripheral surface of the right side inspection drum and the wrong side inspection drum and held on the outer peripheral surface of the drums in a projected state to effect photographing. Therefore, in photographing, no shade is formed on the tablets and no shake occurs, and the tablets are photographed in the state that they are adsorbed and held on the drum surface, allowing positively to obtain clear images, and enabling accomplishment of the visual inspection of the right side and the wrong side of tablets with high accuracy. Further, when the tablets are delivered from the right side inspection drum to the wrong side inspection drum and inverted, the tablets are sandwiched between the rubber band of the right side inspection drum and the rubber band of the wrong side inspection drum. At that time, the tablets are delivered positively without applying a great load to the tablets due to elasticity of both the rubber bands, thus enabling positive delivery and inversion of tablets without damaging the tablets.

Further, since the tablets are adsorbed and held across two rubber bands to be carried, even if the size of the tablets is changed, it is possible to adsorb and hold them without difficulty to carry. Moreover, when the tablets are delivered as described above, the tablets are once sandwiched between the rubber bands making use of elasticity of the rubber bands. Therefore, even if the thickness of tablets is changed, this can be permitted due to the elasticity of the rubber bands not producing an inconvenience such as break, and the tablets can be delivered from the right side inspection drum to the wrong side inspection drum. Consequently, according to this visual inspection apparatus, even in case of changing tablets to be inspected, the difference in size of tablets can be permitted. It is possible to inspect various tablets different in size (diameter and thickness) without replacing the right side inspection drum and the wrong side inspection drum.

Although not particularly limited, preferably, the rubber band is fitted in a band mounting groove formed in the outer peripheral surface of the drum and mounted in a state projected from the outer peripheral surface of the drum, a recess for flexure is formed in the band mounting groove in which recess the depth of the groove is partly deepened corresponding to the suction hole formed in the drum, and a flexure allowance of the rubber band is formed under the rubber band corresponding to each suction hole by the recess for flexure. With this, the load or shock applied to the tablets when the tablets are delivered between the drums can be lessened to positively prevent the break of tablets, and it is possible to highly correspond to the change in size of tablets.

More specifically, by the provision of the flexure allowance under the rubber band as described above, when assuming a state that the tablets are sandwiched between the rubber band of the right side inspection drum and the rubber band of the wrong side inspection drum at the time when the tablets are delivered from the right side inspection drum to the wrong side inspection drum, the rubber bands having the tablets sandwiched therebetween are flexed each other since the flexure allowance of the rubber bands resulting from the recess for flexure provided under both the rubber bands, so that the delivery of the tablets is carried out without applying a great load to the tablets and more positively. As a result, the delivery and inversion operation of the tablets can be carried out more positively without breaking the tablets. Moreover, even in the case where tablets different in thickness are inspected, the rubber bands are flexed due to the flexure allowance provided under the rubber bands as described above whereby even if the thickness of the tablets is changed, this can be permitted positively and no inconvenience such as break occurs, so that the tablets can be delivered from the right side inspection drum to the wrong side inspection drum. Accordingly, in the case where tablets to be inspected are changed, the difference in size of tablets can be permitted with high degree and positively, and tablets different in size (diameter and thickness) can be inspected more positively without the necessity of replacing the right side inspection drum and the wrong side inspection drum.

BRIEF DESCRIPTION OF THE DRAWINGS

FIGS. 4A and 4B are enlarged view showing a state that tablets are held on the side inspection drum, (A) being a plan view, and (B) being a sectional view;

FIGS. 5A, 5B, 5C and 5D are enlarged sectional view sequentially explaining the operation when tablets are shifted from the side inspection drum of the visual inspection apparatus to an attitude conversion drum, the tablets are converted in attitude from an upright attitude to a prostrated attitude, and the tablets are carried from the attitude conversion drum;

FIG. 7 is a perspective view showing an outer tube drum of the right side inspection drum and the wrong side inspection drum constituting the right side and the wrong side inspection section of the visual inspection apparatus;

FIGS. 8A and 8B are fragmentary enlarged view showing an outer peripheral surface portion of an outer tube drum of the right side inspection drum and the wrong side inspection drum constituting the right side and the wrong side inspection section of the visual inspection apparatus, (A) being a perspective view, and (B) being a plan view;

FIGS. 9A and 9B are fragmentary enlarged sectional view showing a state that tablets are held on the outer peripheral surface of an outer tube drum of the right side inspection drum and the wrong side inspection drum constituting the right side and the wrong side inspection section of the visual inspection apparatus, (A) being a cross sectional view, and (B) being a longitudinal sectional view;

DESCRIPTION OF THE PREFERRED EMBODIMENTS

Embodiments of the present invention will be explained in detail hereinafter with reference to the accompanying drawings.

Figure 1:
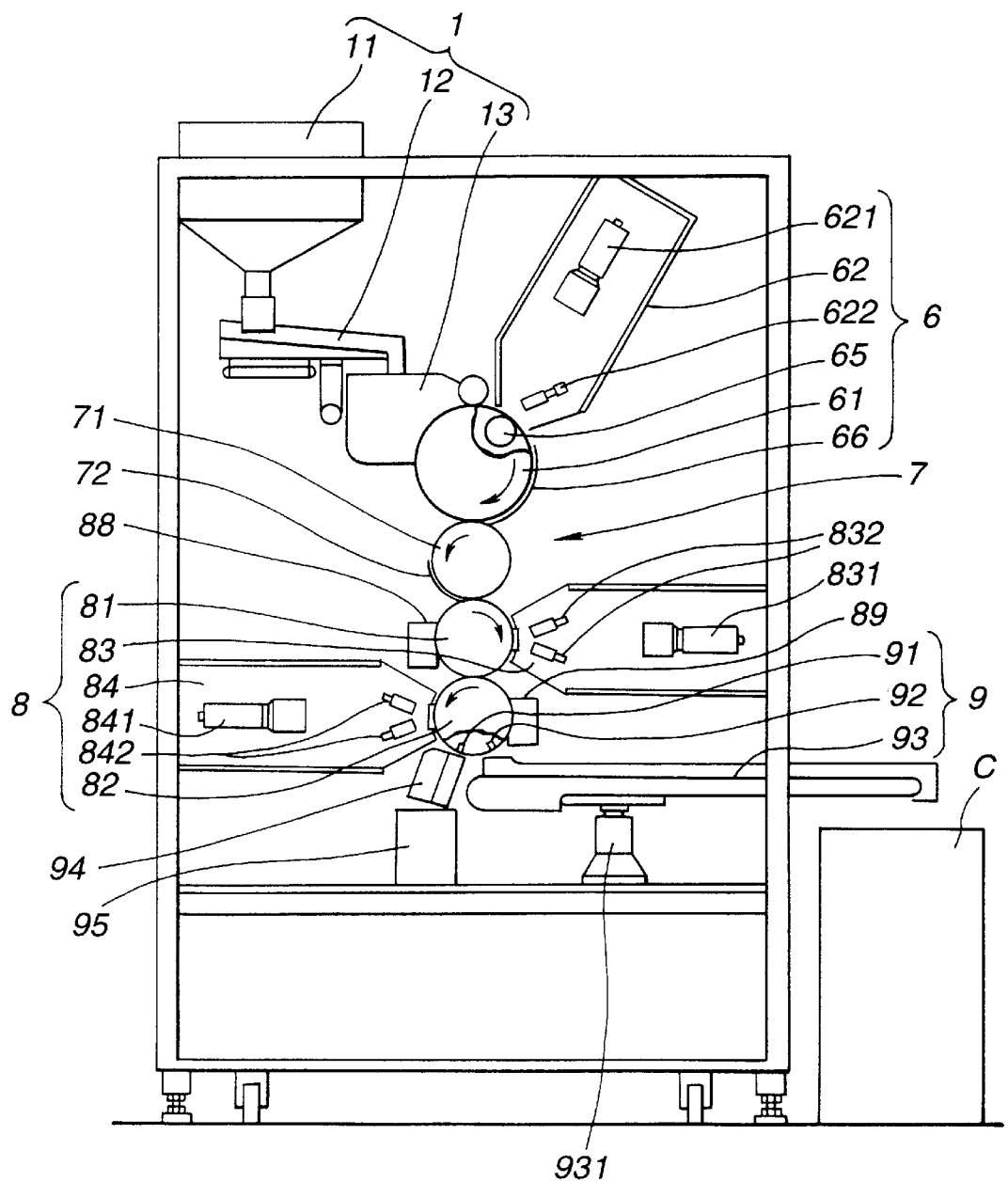
FIG. 1 is a schematic view showing a visual inspection apparatus for tablets according to an embodiment of the present invention.

FIG. 1 shows a visual inspection apparatus for tablets according to one embodiment of the present invention. The visual inspection apparatus comprises a tablet supply section 1 for supplying a number of tablets stored in a hopper 11 to an inspection mechanism, a side inspection section 6 comprising a side inspection drum 61 and a side imaging device 62, an attitude conversion section 7 having an attitude conversion drum 71, a right side and a wrong side inspection section 8 having a right side inspection drum 81, a wrong side inspection drum 82, a right side imaging device 83 and a wrong side imaging device 84, a classification section 9 having a rejected article discharge nozzle 91 and an excellent article discharge nozzle 92 disposed within the wrong side inspection drum 82 and an excellent article recovery conveyor 93, and a decision section (particularly not shown) for processing images taken by said three imaging devices 62, 83 and 84 to detect the presence or absence of appearance defects.

The supply section 1 is designed so that tablets to be inspected stored in the hopper 11 are feed into a supply machine 13 at fixed speeds by a vibration feeder 12, and the tablets are supplied in an upright state from the supply machine 13 to a side inspection drum 61 of the side inspection section 6.

The side inspection section 6 is designed so that the tablets supplied from the supply section 1 are held on the outer peripheral surface of the side inspection drum 61 An a upright state, the tablets are carried downward while keeping their upright state by intermittent rotation of the side inspection drum 61. The tablets are delivered to the attitude conversion section 7 and are photographed by the side imaging device 62 while rotating the tablets in the midst of carriage thereof to take side images of the tablets.

Figure 2:
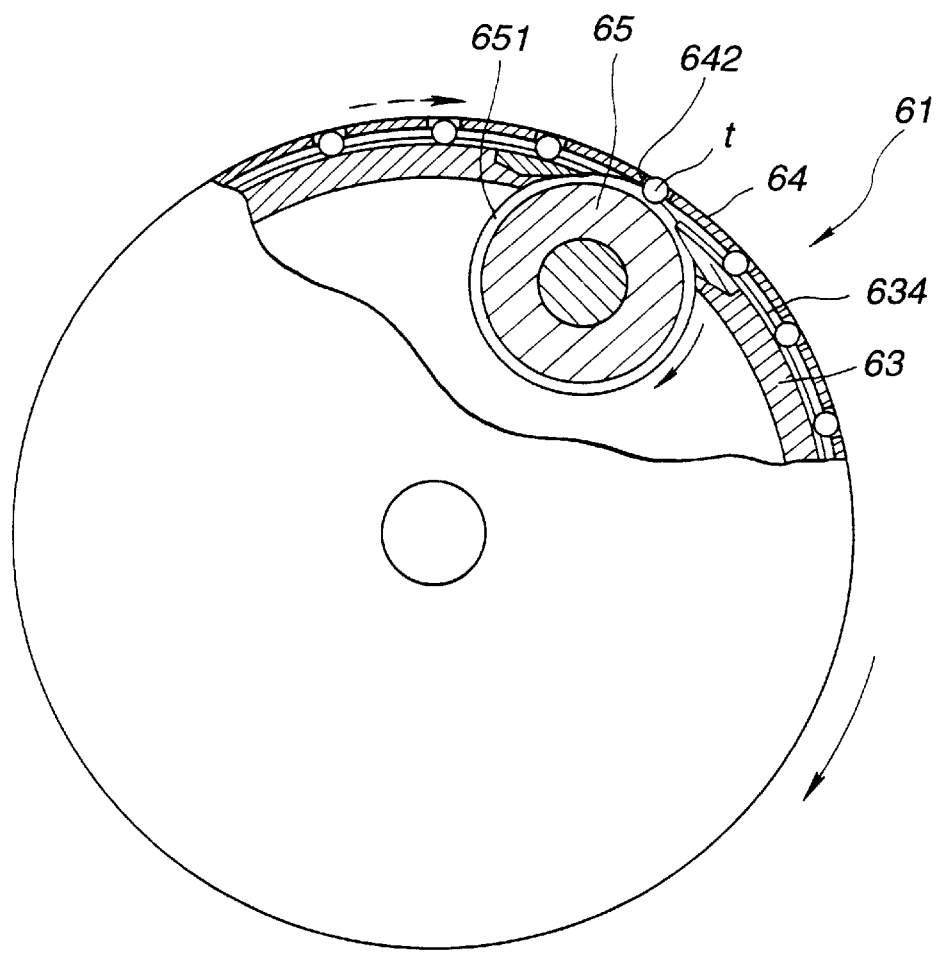
FIG. 2 is a side view partly in section showing a side inspection drum of a side inspection apparatus constituting a side inspection section of the visual inspection apparatus.
Figure 3:
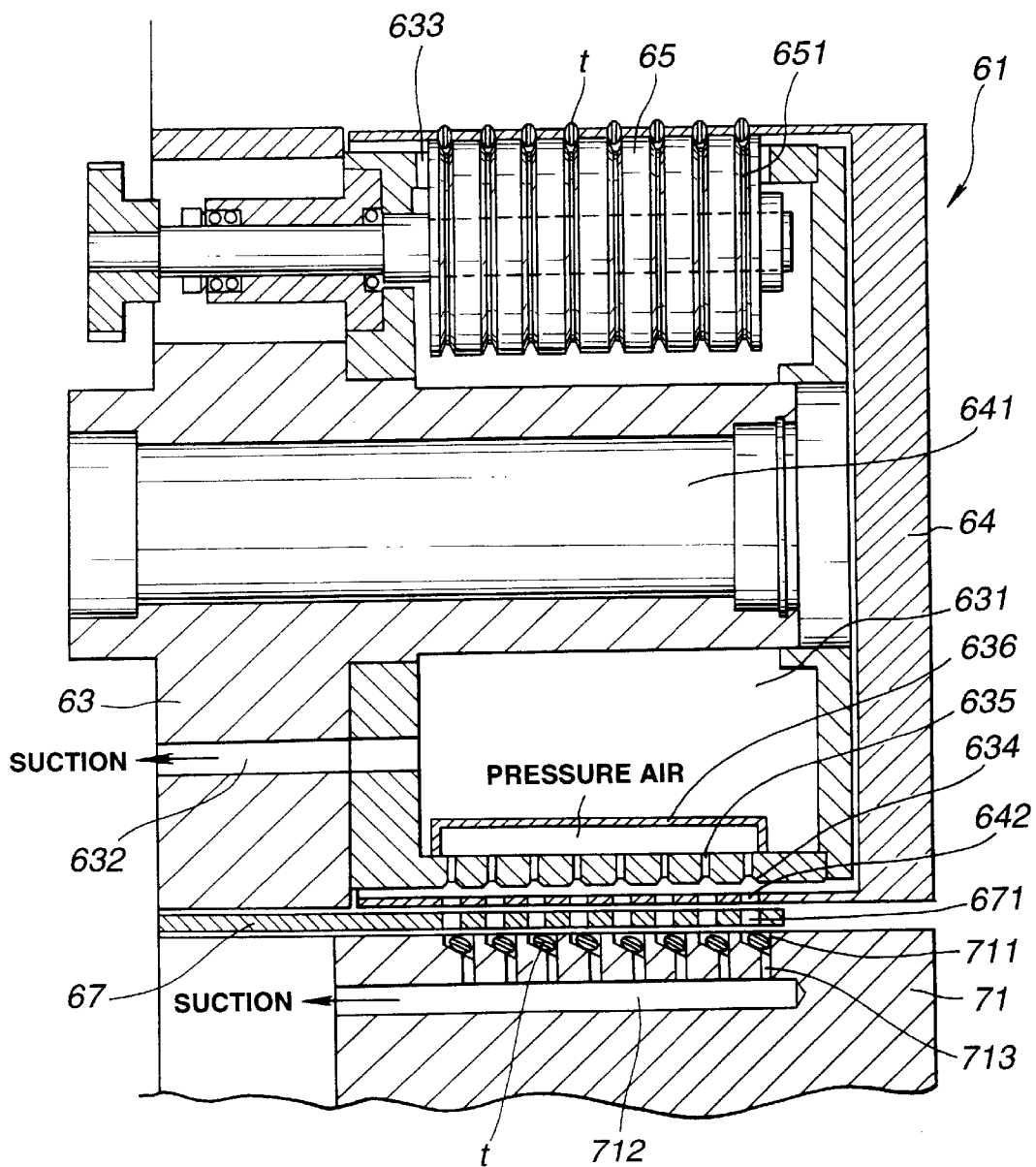
FIG. 3 is a sectional view showing the side inspection drum.

The side inspection drum 61 constituting the side inspection section 6 is composed of an inner tube element 63 secured to the apparatus main body and an outer tube element 64 disposed externally of the inner tube element 63 for intermittent rotation, as shown in FIGS. 2 and 3.

The inner tube element 63 is internally formed with a cavity 631 along the peripheral surface, and the cavity 631 is placed in reduced pressure state by vacuum suction from a suction passage 632. Further, on a part of the cavity is rotatably disposed on a rotating roller 65 in which a groove 651 in V-shape section is formed on the outer peripheral surface thereof corresponding to a holding pocket 642 of the outer tube element 64 described later, and a part of the outer peripheral surface of the rotating roller 65 is exposed from a through-window 633 formed in the peripheral wall of the inner tube element 63 to the outer peripheral surface of the inner tube element 63. Further, the inner tube element 63 is formed in the outer peripheral surface thereof with a guide groove 634 in the peripheral direction corresponding to the holding pocket 642 of the outer tube element 64 described later. The guide groove 634 is provided with a pore 635 at a location where tablets t are delivered to the attitude conversion drum 71 described later, and pressure air is jetted from a pressure air supply chamber 636 communicated with the pore 635 into the guide groove 634.

The outer tube element 64 disposed externally of the inner tube element 63 is driven by a driving shaft 641 and intermittently rotates along the outer peripheral surface of the inner tube element 63, and a number of holding pockets 642 in the form of a through-hole are arrayed and formed on the peripheral wall thereof. The holding pocket 642 is substantially in the shape of a baseball home base in which one end side 642a along the peripheral direction of the outer tube element 64 is formed in a V-shape. In the present embodiment, the V-shaped end 642a and the rotational direction of the outer tube element 64 are coincided. As shown in FIG. 1, a lower portion of about half peripheral portion for carrying tablets of the outer tube element 64 is covered by a cover plate 66 disposed along the outer peripheral surface of the outer tube element 64, and the cover plate 66 prevents tablets t being carried from being dropped down from the holding pocket 642. Further, as shown in FIG. 3, a connection plate 67 continuous from the cover plate 66 is disposed between the outer tube element 64 and the attitude conversion drum 71 described later, and the connection plate 67 is formed with a connection groove 671 in the form of a comb-teeth corresponding to the holding pocket 642.

The side imaging device 62 constituting the side inspection section 6 comprises a camera 621 and an illuminating device 622, and is provided at a position in which the rotating roller 65 of the side inspection drum 61 is disposed to photograph the tablets by the camera 621 while illuminating the surface of the outer tube element 64 by the illuminating device 622 whereby taking images of the whole sides of the tablets t which are held on the holding pocket 642 and rotate on the rotating roller 65.

The attitude conversion section 7 receives the tablets t in the upright state from the side inspection drum 61 of the side inspection section 6 and converts in attitude to the prostrated state to deliver the tablets to the right side inspection drum 81 of the right side and wrong side inspection section 8 described later. As shown in FIG. 1, the attitude conversion section 7 is composed of an attitude conversion drum 71 disposed in a state with the outer peripheral surface whereof placed close to the lower side of the side inspection drum 61 and which rotates at fixed speeds, and a cover plate 72 disposed along the outer peripheral surface of the attitude conversion drum 71.

Figure 6:
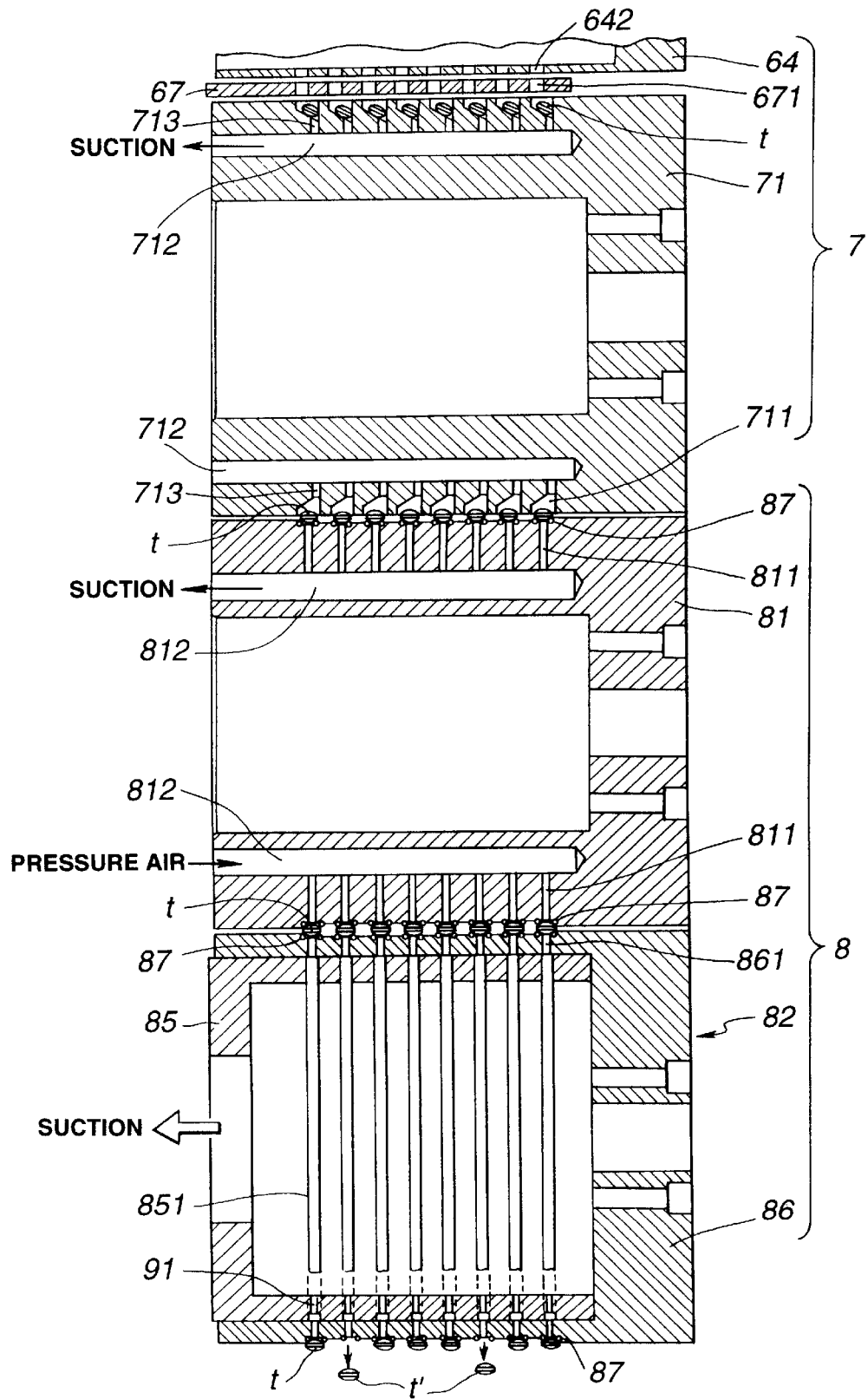
FIG. 6 is a sectional view showing an attitude conversion apparatus constituting an attitude conversion section of the visual inspection apparatus, and a right side and a wrong side inspection section of the visual inspection apparatus.

The attitude conversion drum 71 is formed in the outer peripheral surface thereof with a number of attitude conversion pockets 711 which are arranged corresponding to the holding pockets 642 provided on the outer tube element 64 of the side inspection drum 61, as shown in FIG. 6. Further, the attitude conversion drum 71 is formed in the outer peripheral wall thereof with suction passages 712 in an axial direction corresponding to rows of the attitude conversion pockets 711, and the suction passages 712 are communicated with each one of the attitude conversion pockets 711 through suction holes 713. The suction passages 712 are registered with vacuum suction holes provided in the apparatus main body between the range of the portion receiving the tablets t from the side inspection drum 61 and the position at where the cover plate 72 is disposed so that the attitude conversion pockets 711 are sucked through the suction passages 712 and the suction holes 713, and in other portions, no such suction is carried out.

The attitude conversion pocket 711 has substantially a rectangular shape or an elliptic shape in its plane shape, and the bottom thereof is inclined downward from one end toward the other, as shown in FIGS. 5A, 5B, 5C and 5D and the bottom of the other end is formed with the suction hole 713. The attitude conversion pocket 711 is provided corresponding to the side inspection pocket 642, but as shown in FIGS. 5A, 5B, 5C and 5D, the side inspection pocket 642 is communicated with one end side of the attitude conversion pocket 711 through the connection groove 671 of the connection plate 67.

The cover plate 72 disposed along the outer peripheral surface of the attitude conversion drum 71 is disposed so as to cover, along the peripheral surface of the attitude conversion drum, the lower portion of the half peripheral portion from reception of tablets from the side inspection drum 61 to delivery thereof to the right side inspection drum 81 described later out of the outer peripheral surface of the attitude conversion drum 71 to thereby prevent the tablets t stored in the attitude conversion pockets 711 from being dropped down.

The right side and wrong side inspection section 8 holds the tablets t converted in attitude to the prostrated state by the attitude conversion drum 71 on the outer peripheral surface of the surface inspection drum 81 whose outer peripheral surface is placed in a state close to the lower side of the attitude conversion drum 71 and which rotates at the same peripheral speed as the attitude conversion drum 71. The tablets t are photographed by the right side imaging device 83 to take the right side images of the tablets t. The tablets t are then delivered to the wrong side inspection drum 82 whose outer peripheral surface is placed in a state close to the lower side of the right side inspection drum 81 and which rotates at the same peripheral speed as the right side inspection drum 81, the tablets t are held in the inverted state on the outer peripheral surface of the wrong side inspection drum 82 to be carried, and the tablets t are photographed by the wrong side imaging device 84 to take the wrong side images of the tablets t to thereby carry out the visual inspection of the right sides and wrong sides of the tablets t.

The right side inspection drum 81 is formed in the outer peripheral surface thereof with a number of suction holes 811 in an arrayed state corresponding to the attitude conversion pockets 711 provided on the attitude conversion drum 71, as shown in FIG. 6. Further, the right side inspection drum 81 is formed in the outer peripheral wall thereof with suction/pressure air passages 812 in an axial direction corresponding to rows of the suction holes 811, the suction/pressure air passages 812 being communicated with the suction holes 811. The suction/pressure air passages 812 are registered with vacuum suction holes (not shown) provided on the apparatus main body from the portion for receiving the tablets t from the attitude conversion drum 71 to the portion immediately before the delivery of the tablets t to the wrong side inspection drum 82. The suction holes 811 are sucked through the suction/pressure air passages 812, and at the portion for delivering the tablets t to the wrong side inspection drum 82, the suction/pressure air passages 812 are registered with pressure air emitting holes (not shown) provided on the apparatus main body, and the pressure air is emitted from the suction holes 811 through the suction/pressure air passages 812.

The wrong side inspection drum 82 is composed of an inner tube drum 85 secured to the apparatus main body and an outer tube drum 86 disposed externally of the inner tube drum 85 so as to rotate at the same peripheral speed as the right side inspection drum 81, as shown in FIG. 6. The outer tube drum 86 is formed with a number of suction holes 861 extending through the peripheral wall thereof in a state being arrayed corresponding to the suction holes 811 provided on the right side inspection drum 81. On the other hand, the inner tube drum 85 is formed with suction grooves 851 in a peripheral direction corresponding to the suction holes 861 of the outer tube drum 86. The suction grooves 851 extend through the peripheral wall of the inner tube drum 85 from the portion for receiving the tablets t from the right side inspection drum 81 to the portion in the vicinity of the lower portion of the inner tube drum 85 for classifying the tablets t between excellent articles and rejected articles, and do not extend through the peripheral wall at the lower portion of the inner tube drum 85 for carrying out the classification with the shape of closed-end grooves opened merely to the outer peripheral surface of the inner tube drum 85. The inner tube drum 85 is always vacuum sucked inside, and the suction holes 861 of the outer tube drum 86 are sucked through the suction grooves 851.

As shown in FIGS. 7 to 9, rubber bands 87 circular in section are peripherally wound around the right side inspection drum 81 and the outer tube drum 86 of the wrong side inspection drum 82 with the suction holes 811, 861 sandwiched on the outer peripheral surfaces thereof. That is, as shown in FIGS. 8A and 8B, the right side inspection drum 81 and the outer tube drum 86 are formed in the outer peripheral surfaces with a plurality of band mounting grooves 871, 871 in a peripheral direction with the suction holes 811, 861 sandwiched thereof. As shown in FIGS. 9A and 9B, the rubber bands 87 are fitted in and secured to the band mounting grooves 871, 871, and the rubber bands 87 are mounted to be projected from the outer peripheral surfaces of the right side inspection drum 81 and the outer tube drum 86. Further, as shown in FIGS. 8A and 8B, the band mounting groove 871 is formed with a recess for flexure 872 which is partly deepened in depth corresponding to the forming portions of the suction holes 811, 861. As shown in FIGS. 9A and 9B, a flexure allowance of the rubber band 87 is formed under the rubber band 87 by the recess for flexure 872.

Both the right side inspection drum 81 and the wrong side inspection drum 82 constituting the right side and wrong side inspection section 8 hold the tablets in the prostrated state on the surfaces thereof to carry them. In this case, as shown in FIGS. 9A and 9B, the suction holes 811, 861 of the right side inspection drum 81 and the outer tube drum 86 of the wrong side inspection drum 82 are in the suction state by the aforementioned mechanism, so that the tablets t are adsorbed and held across the two rubber bands 87, 87 disposed with the suction holes 811, 861 sandwiched thereof, in which state the tablets t are carried by the rotation of the right side inspection drum 81 and the outer tube drum 86. The images of the right side and the wrong side of the tablets t are taken by the right side imaging device 83 and the wrong side imaging device 84 in the midst of carriage to effect the visual inspection of the right side and the wrong side. Note, the right side imaging device 83 is composed of the camera 831 and two illuminating devices 832, and the wrong side imaging device 84 is likewise composed of the camera 841 and two illuminating devices 842. Further, in FIG. 1, reference numerals 88, 89 designate recovering cans for recovering rejected tablets which were not well moved to the succeeding step.

At the lower part of the inner tube drum 85 of the wrong side inspection drum 82, there is formed by each suction groove 851, with a rejected article discharge nozzle 91 communicated with the suction groove 851 formed on the inner tube drum 85, as shown in FIG. 6. Although not shown, a pressure air flowing pipe is connected to each rejected article discharge nozzle 91, so that pressure air is emitted from the rejected article discharge nozzle 91 as occasion calls according to the decision of the conditions of articles. Further, as shown in FIG. 1, the inner tube drum 85 of the wrong side inspection drum 82 is formed with a similar excellent article discharge nozzle 92 communicated with each suction groove 851 located downstream in the carrying direction from the rejected article discharge nozzle 91. The excellent article discharge nozzle 92 always emits pressure air despite the decision of the conditions of articles.

Under the wrong side inspection drum 82, there are disposed, as shown in FIG. 1, a rejected article recovering can 95 for receiving and recovering rejected tablets discharged from the wrong side inspection drum 82 by pressure air emitted from the rejected article discharge nozzle 91, a rejected article discharge chute 94 for guiding the rejected tablets to the rejected article recovering can 95 and an excellent article recovering conveyor 93 for carrying excellent tablets discharged from the wrong side inspection drum 82 by pressure air emitted from the excellent article discharge nozzle 92 to outside of the apparatus and charging them into a recovering container c.

The rejected article discharge chute 94 has its internal upper portion divided into a plurality of sections corresponding to the rejected article discharge nozzles 91, though not particularly shown, and a discharge detection sensor formed from a pair of light projector-receivers is disposed at every division so that the discharge of rejected tablets is confirmed by the discharge detection sensor. Further, the excellent article recovering conveyor 93 is supported by a rotational shaft 931 which is rotated by an air cylinder (not shown). In the case where the discharge of the rejected tablets could not be confirmed by the discharge detection sensor despite the rejected tablets were detected, the air cylinder is actuated so that the excellent article recovering conveyor 93 swings so as to charge all the tablets not into the recovering container c but into other recovering containers.

Further, although not particularly shown, the presented visual inspection apparatus is provided with a quality decision section which processes side images, right side images and wrong side images of tablets taken by the imaging devices 62, 83 and 84 to detect appearance defects such as adhesion of foreign matter and contamination or break and crack to perform the quality decision, and controls emission of pressure air from the rejected article discharge nozzle 91 according to the result of decision.

The operation of the visual inspection apparatus according to the present embodiment will be explained hereinafter.

In the visual inspection apparatus according to the present embodiment, a number of tablets are charged into the apparatus through the hopper 11 (see FIG. 1), the visual inspection for the sides, right sides and wrong sides of the tablets is continuously carried out, and rejected tablets having appearance defects such as adhesion of foreign matter to either of the sides, right sides and wrong sides and contamination or break and scratches and excellent tablets without appearance defects are classified and recovered.

First, the tablets supplied at random from the hopper 11 are charged into the supply machine 13 at fixed speeds by the vibration feeder 12, and the tablets are sequentially and continuously charged in the upright state into the holding pockets 642 formed in the outer tube element 64 of the side inspection drum 61 of the side inspection section 6.

The tablets t stored in the side inspection pockets 642 of the outer tube element 64 of the side inspection drum 61 are carried downward while rolling on the outer peripheral surface of the inner tube element 63 maintaining the upright state by the intermittent rotation of the outer tube element 64, as shown in FIG. 2. At this time, the tablets t are stably carried in the upright attitude on the fixed track along with the guide groove 634 formed in the outer peripheral surface of the inner tube element 63. When carried to the position at which the rotating roller 65 of the inner tube element 63, the tablets t are run on the rotating roller 65 and inserted into the V-shaped grooves 651 of the rotating roller 65, in which state the outer tube element 64 intermittently stops, and the tablets t rotate at fixed speeds while maintaining the upright state held in pockets 642 by the rotation of the rotating roller 65. The carriage intermittently stops so that the tablets which rotate in the upright state are photographed by the side imaging device 62 to take images of the whole sides of the tablets t.

In this case, in the side inspection section 6 of the visual inspection apparatus according to the present embodiment, the holding pocket 642 provided on the outer tube element 64 has one end 642a side formed into a baseball home base in a V-shape, as shown in FIGS. 4B, and 4B, and the rotating roller 65 is formed in the outer peripheral surface with the groove 651 in a V-shaped in section in a peripheral direction corresponding to the position at which the holding pocket 642 is formed so that the rotating roller 65 is rotatable toward the V-shaped end 642a side of the holding pocket 642 whereby the tablets t can be rotated extremely stably keeping the upright state. Even sugar-coated tablets whose peripheral edge is formed to be round, it is possible to take images while rotating them in the upright attitude in an extremely stable manner and perform the side inspection with high accuracy. Further it is possible to permit changes in size of tablets t.

That is, in the side inspection section 6 of the visual inspection apparatus according to the present embodiment, when the tablets t are rotated on the rotating roller 65, the tablets t are inserted into the V-shaped groove 651 of the rotating roller 65 in which state the tablets t rotate so as to be rolled along the V-shaped groove 651. Thus, the tablets t can be rotated much more stably than the case where the tablets t rotate so as to be rolled on the roller surface in the state that the tablets t are merely placed on the roller surface without a V-shaped groove. Even sugar-coated tablets whose peripheral edge is formed to be round, both sides thereof are respectively placed in contact with both inner sides of the V-shaped groove 651 whereby the tablets t can be rotated very stably. Moreover, since the rotating roller 65 is rotated toward the V-shaped end 642a of the holding pocket 642, the tablets t rolling on the rotating roller 65 are brought near to the V-shaped end 642a of the holding pocket 642 (see FIG. 4A). Therefore, even sugar-coated tablets whose peripheral edge is formed to be round, both sides thereof are respectively placed in contact with both inner surfaces of the V-shaped end 642a whereby the tablets t can be rotated very stably while maintaining an extremely stable upright state.

Since as described above, the rotating tablets t come near to the V-shaped end 642a of the holding pocket 642, by forming the holding pocket 642 relatively large, even if the size of the tablets t is changed, both sides of the tablets t can be positively supported by the V-shaped end 642a which gradually narrows to the end to obtain the stable upright state. In addition, since the tablets t rotate in the state of being inserted into the V-shaped groove 651 of the rotating roller 65, even if the thickness of the tablets t is changed, tablets t can be rotated being positively held within the V-shaped groove 651. Consequently, according to the side inspection section 6, even in the case where the tablets t to be inspected are changed, it is possible to permit the difference in size of the tablets t, and possible to inspect various tablets different in size (diameter and thickness) without necessity of replacing the side inspection drum 61.

The tablets t subjected to photographing of the side thereof are sequentially fed downward by the intermittent rotation of the outer tube element 64 after taking images and transferred to the attitude conversion pockets 711 formed on the attitude conversion drum 71 of the attitude conversion section 7. And the tablets t are converted in attitude from the upright state to the prostrated state within the attitude conversion pockets 711.

The delivery of the tablets t from the side inspection drum 61 to the attitude conversion drum 71 and the attitude conversion by the attitude conversion drum 71 are carried out in the following manner. The tablets t are held within the holding pockets 642 of the outer tube element 64 of the side inspection drum 61 and carried to the lowest portion of the side inspection drum 61. Then, as shown in FIG. 5A, the small pores 635 of the inner tube element 63, the holding pockets 642 of the outer tube element 64, the connection grooves 671 of the connection plate 67, and the attitude conversion pockets 711 of the attitude conversion drum 71 are arrayed in a row in a vertical direction. In this state, the pressure air is emitted through the small holes 635 from the pressure air supply chamber 636 (see FIG. 3) provided on the lowest portion of the inner tube element 63, and the attitude conversion pockets 711 of the attitude conversion drum 71 are sucked through the suction passage 71 and the suction holes 713. The tablets t are discharge from the holding pockets 642 of the outer tube elements 64 due to the pressure air, the suction and their own weight, as shown in FIG. 5B and fed in the upright state to one end side of the attitude conversion pockets 711 of the attitude conversion drum 71 through the connection grooves 671 of the connection plate 67. As shown in FIG. 5C, the tablets t are slidably moved from one end side to the other end side of the pockets 711 by the inclination of the bottom surface of the attitude conversion pockets 711 and the suction from the suction holes 713 provided on the other end portion so that the tablets t are converted in attitude from the upright state to the prostrated state. The tablets t are carried downward by the rotation of the attitude conversion drum 71 while they are stored in the attitude conversion pockets 711. At this time, the suction state within the attitude conversion pockets 711 is released after receiving the tablets t, and as shown in FIG. 5D, the tablets t stored in the attitude conversion pockets 711 are slidably carried in the complete prostrated state on the inner peripheral surface of the cover plate 72 (see FIG. 1) disposed along the outer peripheral surface of the attitude conversion drum 71.

As described above, the attitude conversion section 7 has the bottom surface inclined downward from one end to the other end. The tablets t in the upright state are received from the side inspection drum 61 on one end side of the attitude conversion pockets 711 having the suction holes 713 on the bottom surface of the other end portion, and the tablets t are slidably moved on the bottom surface from one end side to the other end side of the pockets 711 by the inclination of the bottom surfaces of the pockets 711 and the suction from the suction holes 713 provided on the other end portion whereby the tablets t are converted in attitude from the upright state to the prostrated state. With this constitution, the tablets t are converted in attitude from the upright state to the prostrated state naturally and smoothly along the inclination of the bottom surface of the attitude conversion pockets 711 so that the great load or shock is not applied to the tablets without the inconveniences such as crack, break and so on, and the tablets t can be converted in attitude from the upright state to the prostrated state positively.

Further, since the attitude conversion section 7 causes the tablets t to slide on the inclined bottom surfaces of the attitude conversion pockets 711 to convert the attitude of the tablets, as described above, it is not necessary to strictly locate the tablets t as in the case of using the attitude conversion grooves of the guide plate. Therefore, even if the attitude conversion pockets 711 are considerably larger than the tablets t, the attitude conversion is carried out without any problems. Consequently, the attitude conversion pockets 711 are made larger to some extent to thereby cope with various sizes of the tablets. According to the attitude conversion section 7, even when the tablets to be inspected are changed, it is possible to permit the difference in size of the tablets and possible to inspect various tablets different in size (diameter and thickness) without requiring replacement of the attitude conversion drum 71.

The tablets t converted in attitude from the upright state to the prostrated state within the attitude conversion pockets 711 are delivered to the right side inspection drum 81 of the right side and wrong side inspection section 8 at the lowest portion of the attitude conversion drum 71, as shown in FIG. 6. At this time, the tablets t stored in the attitude conversion pockets 711 to be carried to the lowest portion of the attitude conversion drum 71 are slidably carried in the complete prostrated state on the inner peripheral surface of the cover plate 72 (see FIG. 1) disposed along the outer peripheral surface of the attitude conversion drum 71, as described above, and positively supplied to the right side inspection drum 81 in the complete prostrated state.

The tablets t transferred from the attitude conversion drum 71 to the right side inspection drum 81 are transferred onto the two rubber bands 87 wound around on the outer peripheral surface of the right side inspection drum 81 from the attitude conversion pockets 711 with the suction holes 811 sandwiched by the suction of the suction holes 811, in the state that the attitude conversion pockets 711 of the attitude conversion drum 71 are registered with the suction holes 811 of the right side inspection drum 81, as shown in FIG. 6. As a result, the tablets t are adsorbed on the rubber bands 81. The tablets t are then carried downward by the rotation of the right side inspection drum 81 in the state that each of them are adsorbed across the two rubber bands 87, 87 of the right side inspection drum 81 as shown in FIGS. 9A and 9B. The right side images of the tablets t are taken by the right side imaging device 83 in the midst of carriage, and the tablets are delivered to the wrong side inspection drum 82 at the lowest portion of the right side inspection drum 81.

Figure 10:
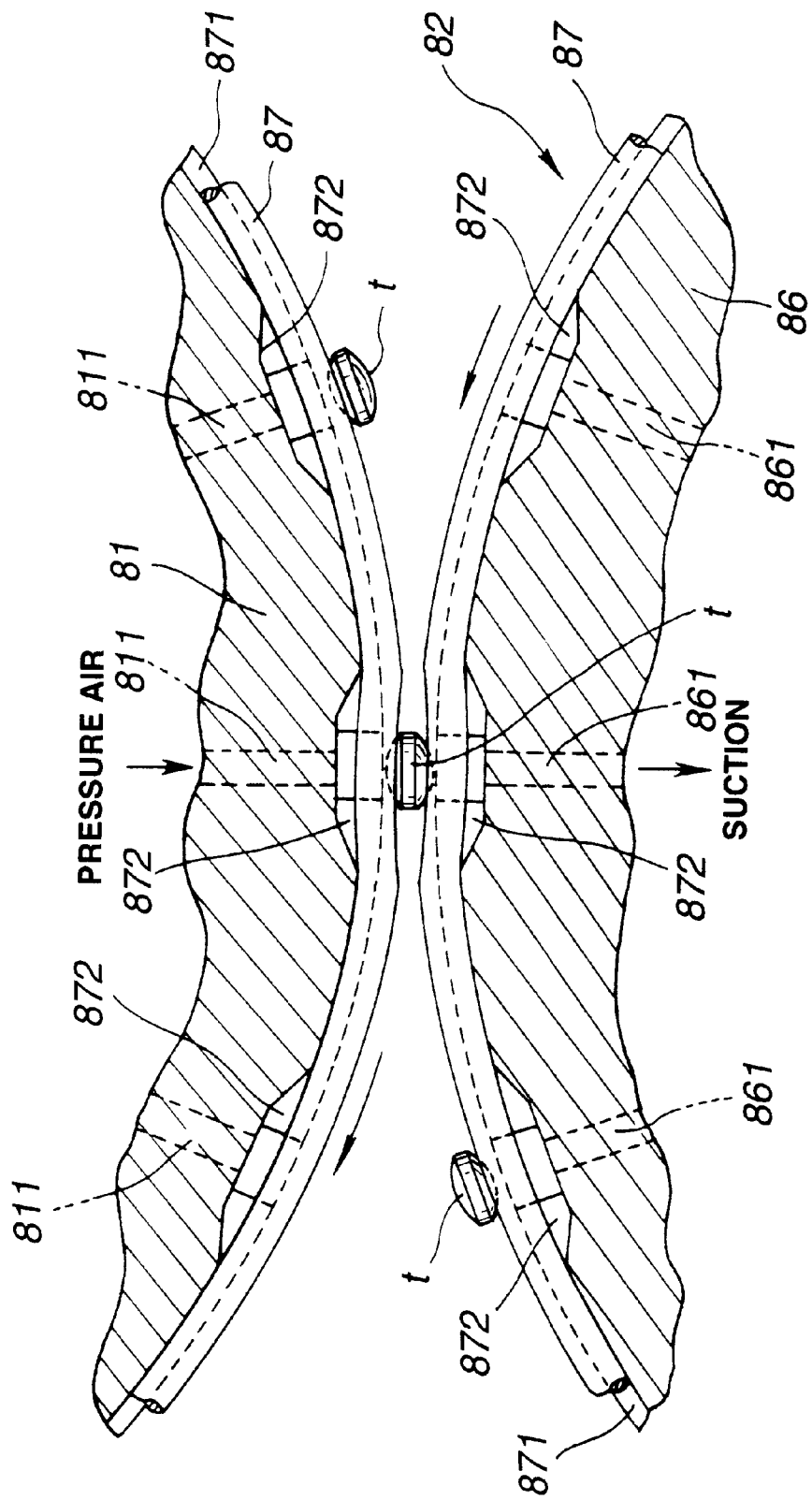
FIG. 10 is an enlarged sectional view showing a portion for delivering tablets from the right side inspection drum to the outer tube drum of the wrong side inspection drum in the right side and the wrong side inspection section of the visual inspection apparatus.

The delivery of the tablets t from the right side inspection drum 81 to the wrong side inspection drum 82 is carried out in the following manner. As shown in FIG. 10, the suction holes 811 of the right side inspection drum 81 are registered with the suction holes 861 provided in the outer tube drum 86 of the wrong side inspection drum 82 with the tablets t carried to the lowest portion of the right side inspection drum 81 sandwiched, and at this time, the tablets t are sandwiched between the rubber band 87 wound around the right side inspection drum 81 and the rubber band 87 wound around the outer tube drum 86 of the wrong side inspection drum 82. Then, pressure air is emitted from the suction holes 811 of the right side inspection drum 81 so that the suction holes 861 provided in the outer tube drum 86 of the wrong side inspection drum 82 assumes the suction state, and the tablets t are transferred from the right side inspection drum 81 to the outer tube drum 86 of the wrong side inspection drum 82 and adsorbed on the rubber band 87 of the outer tube drum 86 in the inverted state.

Then, similar to the case of the above-described right surface inspection drum 81, each one of the tablets t is adsorbed across the two rubber bands 87 wound around the outer tube drum 86 of the wrong side inspection drum 82, and in that state, the tablets t are carried downward by the rotation of the outer tube drum 86, and the wrong side images of the tablets t are taken by the wrong side imaging device 84 in the midst of the carriage.

According to the visual inspection of the right sides and wrong sides of the tablets t by the right side and wrong side inspection section 8 as shown in FIGS. 9A and 9B, the tablets t are adsorbed on the rubber bands 87 projected from the outer peripheral surfaces of the right side inspection drum 81 or the outer tube drum 86 of the wrong side inspection drum 82 and held in such a state as projected to the outer peripheral surfaces of the drums 81, 86 for photographing. Therefore, at the time of photographing, the tablets t can be photographed in the state that they are held on the surfaces of the drums 81, 86 without shade or play, thus positively obtaining clear images, and the visual inspection of the right side and wrong side thereof can be carried out with high accuracy. When the tablets t are delivered from the right side inspection drum 81 to the outer tube drum 86 of the wrong side inspection drum 82 for inversion, the tablets t are sandwiched between the rubber band 87 of the right side inspection drum 81 and the rubber band 87 of the outer tube drum 86, as shown in FIG. 10. At this time, since there is provided a flexure allowance for the rubber bands 87 caused by the recess for flexure 872 under both the rubber bands 87, 87. The rubber bands 87, 87 with the tablets sandwiched therebetween become flexed each other so that the delivery of the tablets t is carried out positively without applying a large load to the tablets t, and the delivery of the tablets and inversion operation can be carried out positively without breaking the tablets t.

Further, as shown in FIGS. 9A and 9B, since the tablets t are adsorbed on and held by the two rubber bands 87 to be carried, they can be carried while being adsorbed and held even if the size of the tablets t is changed. Moreover, since the flexure allowance is provided under the rubber bands 87 at places of both the drums 81, 86 where the tablets t are held, even if the thickness of the tablets t is changed, this can be permitted by the flexure of the rubber bands 87. The tablets t can be delivered from the right side inspection drum 81 to the wrong side inspection drum 82 free from inconveniences such as a break. According to the right side and wrong side inspection section 8, even if the tablets t to be inspected are changed, it is possible to permit the difference in size of the tablets t, and possible to inspect various tablets different in size (diameter and thickness) without requiring replacement of the right side inspection drum 81 and the wrong side inspection drum 82.

Next, while the tablets t subjected to taking the right side image and the wrong side image are carried downward by the rotation of the outer tube drum 86 of the wrong side inspection drum 82 after taking images, the quality decision section (not shown) processes the side image, the right side image and the wrong side image to inspect the presence or absence of the external defects of the tablets t. As described in FIG. 6, when the external defect is detected, pressure air is emitted only from the nozzle corresponding to the tablets t¹ which were decided to have the external defect amongst the rejected article discharge nozzles 91, and only the rejected tablets t¹ are blown downward from the outer peripheral surface of the outer tube drum 86 while the other excellent tablets t are further carried by the rotation of the outer tube drum 86. Then, all the tablets t are blown downward from the outer tube drum 86 by the pressure air emitted from the excellent article discharge nozzles 92 (see FIG. 1) and dropped onto the excellent article recovering conveyor 93, by which the tablets t are carried outside of the apparatus and recovered into the recovery container c.

On the other hand, the rejected tablets t¹ discharged from the wrong side inspection drum 82 are recovered into the rejected article recovering can 95 (see FIG. 1) through the rejected article discharge chute 94 (see FIG. 1). At this time, the passage of the rejected tablets t¹ is detected by the discharge detection sensor (not shown) disposed within the rejected article discharge chute 94 so as to confirm the discharge of the rejected tablets t¹ from the wrong side inspection drum 82. In the event that the discharge of the tablets is not confirmed by the discharge detection sensor despite the defects are detected, the air cylinder (not shown) is actuated so that the excellent article recovery conveyor 93 swings to feed all the tablets discharged on the excellent article recovery conveyer 93 not into the recovery conveyor c but into other recovery containers (not shown), preventing the rejected tablets from being mixed into the excellent tablets. It is noted that a group of tablets which possibly mixed with the rejected ones may be again returned to the hopper 11 for inspection.

As described above, in the visual inspection apparatus according to the present embodiment, the drum 61 comprising the holding pockets 642 in the form of a home base having one end side formed into a V-shape and the rotating roller 65 having the V-shaped grooves 651 in the outer peripheral surface thereof is used as the side inspection drum of the side inspection section 6 whereby the tablets t can be rotated extremely stably in the upright attitude. Even the case of the sugar-coated cylinders whose peripheral edge portion is formed to be round, the clear images can be taken while stably rotating them in the upright attitude and the side inspection can be made with high accuracy. Further, the attitude conversion drum 71 having the attitude conversion pockets 711 whose bottom wall is inclined is used as the attitude conversion section 7 to slidably move the tablets t on the bottom surface of the pockets 711 from one end side to the other end side whereby the tablets t are converted in attitude from the upright state to the prostrated state. Therefore, it is possible to positively convert the attitude of the tablets t from the upright state to the prostrated state without applying a large load or shock to the tablets t at the time of converging the attitude and preventing the occurrence of inconveniences such as crack or break if possible. Further, the right side inspection drum 81 and the wrong side inspection drum 82 having the rubber bands 87 wound around the outer peripheral surfaces thereof are used as the right side and wrong side inspection section 8 so that the tablets t are adsorbed and held on the rubber bands 87 and carried so as to take the images whereby clear images can be obtained positively and the visual inspection of the right sides and wrong sides can be carried out with high accuracy. In addition, by the provision of the recess for flexure 872 provided on the right side inspection drum 81 and the outer tube drum 86 of the wrong side inspection drum 82 respectively, the rubber bands 87, 87 with the tablets t sandwiched therebetween assume the state flexed each other when the tablets t are delivered from the right side inspection drum 81 to the wrong side inspection drum 82 whereby the delivery of the tablets t can be carried out positively without applying a large load to the tablets t. Therefore, the delivery of the tablets t and inversion can be carried out positively without breaking the tablets t.

Accordingly, in the visual inspection apparatus according to the present embodiment, it is possible to carry the tablets t positively and stably without breaking the tablets t, and possible to carry out the visual inspection with high accuracy. Even with the sugar-coated cylinder whose peripheral edge portion is formed to be round, it is possible to positively carry out the visual inspection including the sides. Further, as described above, all of the side inspection section 6, the attitude conversion section 7 and the right side and wrong side inspection section 8 of the visual inspection apparatus can correspond changes in the size of the tablets to be inspected without replacing the drums for carrying the tablets and can carry out the visual inspection for various sizes of tablets without requiring cumbersome replacing work of the drums.

Figure 11:
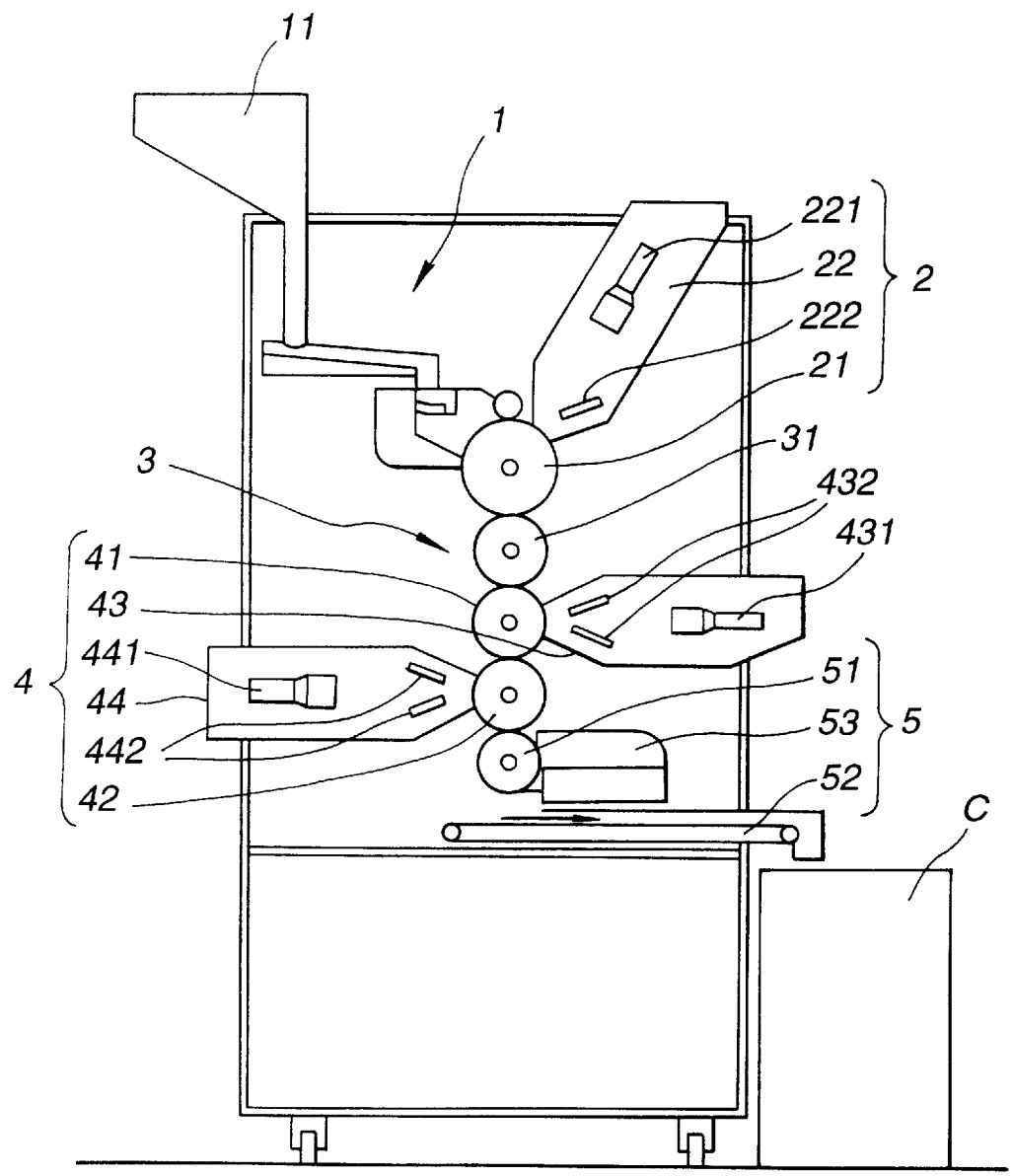
FIG. 11 is a schematic view showing a conventional visual inspection apparatus.
Figure 12:
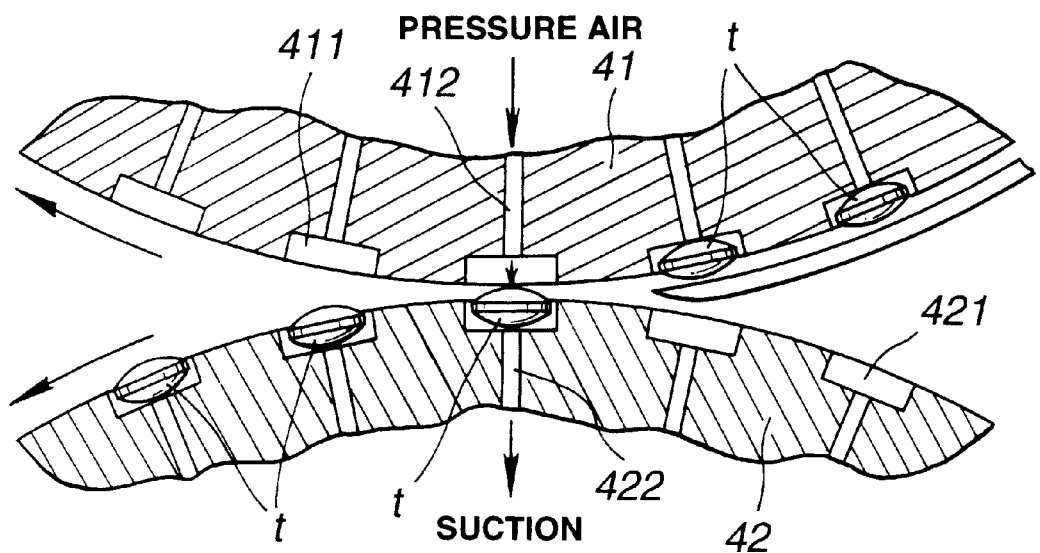
FIG. 12 is a fragmentary sectional view showing the right side inspection drum and the wrong side inspection drum constituting the side inspection section of the visual inspection apparatus.

It is noted that the visual inspection apparatus according to the present invention is not limited to the aforementioned embodiments, but can be variously changed without departing the subject matter of the present invention. For example, the side inspection section 6, the attitude conversion section 7 and the classification section 9 can be modified similarly to the conventional visual inspection apparatus as shown in FIG. 11 or may employ other mechanisms. Further, the side inspection section 6 can be omitted depending on the kind of tablets to be inspected.

As described above, according to the visual inspection apparatus of the present invention, it is possible to stably carry the tablets to positively obtain excellent images. Further, it is possible to carry out a high degree of visual inspection positively and stably without breaking the tablets during the carriage or at the time of delivery between the drums. Also in the case where the kind (size and thickness) of the tablets is changed, it is possible to cope therewith without replacing the right side inspection drum and the wrong side inspection drum.

What is claimed is:

1. A visual inspection apparatus for tablets comprising:

a right side inspection drum for holding flat-shaped tablets on the outer peripheral surface in a prostrated state with the thickness direction vertically set and being rotated at fixed speeds to thereby carry the tablets;

a wrong side inspection drum disposed in the state that the outer peripheral surface thereof is placed close to the right side inspection drum, receiving the tablets from the right side inspection drum to hold the tablets in an inverted state on the outer peripheral surface and being rotated at fixed speeds to carry the tablets;

a right side imaging device for photographing the tablets held on the surface of the right side inspection drum to take the right side image of the tablets; and a wrong side imaging device for photographing the tablets held on the outer peripheral surface of the wrong side inspection drum to take the wrong side image of the tablets;

both the right side inspection drum and the wrong side inspection drum comprising an array of numbers of suction holes and formed on the outer peripheral surfaces of the drums, and a plurality of rubber bands wound along the peripheral direction with the suction holes put therebetween, wherein the tablets are adsorbed across two rubber bands by suction from the suction holes.

2. The visual inspection apparatus for tablets according to claim 1, wherein said rubber bands are fitted in and secured to band mounting grooves formed in the outer peripheral surfaces of the drums and mounted in the state projected from the outer peripheral surfaces of the drums, said mounting grooves being formed with recesses for flexure with the depth of the grooves partly deepened corresponding to said suction holes, and a flexure allowance of the rubber band is formed under the rubber band corresponding to each suction hole.

3. The visual inspection apparatus for tablets according to claim 1, further comprising:

- a tablet supply section for continuously supplying, to an inspection mechanism section with a number of flat-shaped tablets in an upright state with diametrical direction set vertically,
- a side inspection section for carrying the tablets supplied from said tablet supply section in the upright state and taking images of the whole side of said tablets while rotating the tablets in a midst of carriage,
- an attitude conversion section for receiving the tablets in the upright state from said side inspection section, and converting an attitude of the tablets to a prostrated state with the thickness direction set vertically to deliver them to said right side inspection drum,
- a quality decision section for processing images of the side image, the right side image and the wrong side image taken to decide the presence or absence of appearance defects, and
- classification means for classifying and recovering excellent tablets without appearance defects and rejected tablets with appearance defects according to the results of decision by said quality decision section.

4. The visual inspection apparatus for tablets according to claim 1, wherein said wrong side inspection drum comprises an inner tube drum and an outer tube drum rotatably disposed externally of said inner tube drum having said suction holes and said rubber bands, a rejected article discharge nozzle for emitting pressurized air as occasion calls according to a results of decision by a quality decision section and an excellent article discharge nozzle provided downstream in a carrying direction from said rejected article discharge nozzle to always emit pressurized air are disposed lower portion of the inner tube drum as said classification means, whereby the rejected tablets are selectively discharged and recovered from said wrong side inspection drum by the pressurized air emitted as occasion calls from said rejected article discharge nozzle, and the excellent tablets are discharged and recovered from said wrong side inspection drum by the pressurized air always emitted from said excellent article discharge nozzle.

5. The visual inspection apparatus for tablets according to claim 3, wherein said side inspection section comprises an inner tube element, an outer tube element intermittently rotatably disposed externally of said inner tube element and formed in the peripheral wall intermittently rotated along the outer peripheral surface of the inner tube element with a number of through-hole holding pockets, and a rotating roller rotatably disposed internally of said inner tube element and which rotates in a state that a part of the outer peripheral surface thereof is exposed to the outer peripheral surface of the inner tube element from a through-window formed in the peripheral wall of the inner tube element; comprising a side inspection apparatus in which the flat-shaped tablets are stored in the upright state with the diametrical direction vertically set into said holding pockets, the tablets are rolled and carried on the outer peripheral surface of said inner tube element while maintaining them in the upright state in said holding pockets by the intermittent rotation of said outer tube element, the tablets in said holding pockets are rotated on said rotating roller, and the images of the whole periphery of the side of the rotating tablets are taken to thereby detect the appearance defects of the side of the tablets, wherein at least one end side of said holding pockets is formed into a V-shape and grooves having a V-shape in section are formed in the peripheral direction corresponding to positions at which said holding pockets are formed in the outer peripheral surface of said rotating roller, and said rotating roller is rotated toward the V-shaped end side of said holding pockets.

6. The visual inspection apparatus for tablets according to any of claims 3 to 5, wherein said attitude conversion section comprises an attitude conversion drum having a bottom surface inclined downward from one end to the other and formed in the peripheral surface thereof with a number of attitude conversion pockets having a suction hole in the bottom surface of the other end, said side inspection section and said right side inspection section are arranged above and below, respectively, of said attitude conversion drum, the tablets in the upright state are received into said attitude conversion pockets from said side inspection section through one end side of said pockets, the tablets are slidably moved on the bottom surface from one end side to the other end of said pockets by the inclination of the bottom surfaces of said pockets and the suction from the suction holes provided on the other end, the tablets are converted in attitude from the upright state to a prostrated state, and the tablets in the prostrated state are carried downward by the rotation of said attitude conversion drum and supplied to said right side inspection drum in the prostrated state.

7. The visual inspection apparatus for tablets according to claim 6, wherein a lower portion of a semi-peripheral portion from where the tablets are received from said side inspection section to the portion where tablets are delivered to said right side inspection drum on the outer peripheral surfaces of said attitude conversion drum is covered by a cover plate arranged along the peripheral surface of said attitude conversion drum, and the tablets stored in said attitude conversion pockets and carried are slidably moved on the inner peripheral surface of said cover plate.

* * * * *